(12) United States Patent
Kaufman et al.

(10) Patent No.: US 8,329,121 B2
(45) Date of Patent: Dec. 11, 2012

(54) APPARATUS FOR PREPARING CYTOLOGICAL SPECIMENS

(75) Inventors: Howard B. Kaufman, Newton, MA (US); Tuan Ha, Randoiph, MA (US)

(73) Assignee: Hologic, Inc., Marlborough, MA (US)

( * ) Notice: Subject to any disclaimer, the term of this patent is extended or adjusted under 35 U.S.C. 154(b) by 161 days.

(21) Appl. No.: 13/032,517

(22) Filed: Feb. 22, 2011

(65) Prior Publication Data

US 2012/0214227 A1 Aug. 23, 2012

(51) Int. Cl.
*A61B 10/00* (2006.01)
(52) U.S. Cl. .......... 422/536; 422/50; 422/401; 422/547; 436/180
(58) Field of Classification Search .................... 422/50, 422/401, 536, 547; 436/180
See application file for complete search history.

(56) References Cited

U.S. PATENT DOCUMENTS

| | | |
|---|---|---|
| 5,143,627 A | 9/1992 | Lapidus et al. |
| 5,240,606 A | 8/1993 | Lapidus et al. |
| 5,269,918 A | 12/1993 | Lapidus et al. |
| 5,282,978 A | 2/1994 | Polk, Jr. et al. |
| 6,562,299 B1 | 5/2003 | Ostgaard et al. |
| 6,572,824 B1 | 6/2003 | Ostgaard et al. |
| 7,579,190 B2 | 8/2009 | Ostgaard et al. |

*Primary Examiner* — Jyoti Nagpaul
(74) *Attorney, Agent, or Firm* — Vista IP Law Group LLP

(57) ABSTRACT

A handheld apparatus for preparing a specimen slide includes a handle, a filter holder assembly coupled to and extending from the handle; and a slide holder assembly coupled to and extending from the handle spaced apart from the filter holder assembly, wherein the slide holder assembly comprises a plurality of positioning members movably coupled to one another, and a slide holder movably coupled to one of the positioning members to allow a slide mounted on the slide holder to make rolling contact with an outward facing surface of a filter mounted on the filter holder assembly.

32 Claims, 6 Drawing Sheets

APPARATUS FOR PREPARING CYTOLOGICAL SPECIMENS

FIELD

The present invention relates to preparation of cytological specimens and, more specifically, to a manual method and apparatus for preparing a cytological specimen from a patient sample and maintaining one-to-one correlation between the patient sample and the specimen.

BACKGROUND

Cytology is a branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "pap smear" test, in which cells are scraped from a woman's cervix and analyzed in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions may be applied to the cells on the glass slide for preserving the specimen for archival purposes and for facilitating examination.

It is generally desirable that the cells on the slide have a proper spatial distribution, so that individual cells can be examined. A single layer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologist can more readily discern abnormal cells. The cells are also able to be counted to ensure that an adequate number of cells have been evaluated.

Certain methods and apparatus for generating a thin monolayer of cells on a slide advantageous for visual examination are disclosed in U.S. Pat. Nos. 5,143,627, 5,240,606, 5,269,918, 5,282,978, 6,572,824, 6,562,299 and 7,579,190, all of which are assigned to the assignee of the present invention and all of the disclosures of which are incorporated herein by reference in their entirety.

According to one method disclosed in these patents, a patient's cells in a preservative fluid in a sample container are dispersed using a spinning sample collector disposed therein. A controlled vacuum is applied to the sample collector to draw the fluid through a screen filter thereof until a desired quantity and spatial distribution of cells is collected against the filter. Thereafter, the sample collector is removed from the sample container and the filter portion impressed against a glass slide to transfer the particles of interest to the slide in substantially the same spatial distribution as collected.

While apparatus manufactured according to the teachings of one or more of these patents have been commercially successful, such as the ThinPrep® 2000 and ThinPrep® 3000 Systems manufactured and sold by Cytyc Corporation located in Marlborough, Mass., such apparatuses require substantial capital investment and laboratory bench space.

Once a specimen is prepared, fixed, and stained, the specimen may be manually visually inspected by a cytotechnologist, typically under magnification, and with or without various sources of illumination. Alternatively or additionally, automated machine vision systems have been adapted to aid cytological inspection. For example, an automated vision system may perform a preliminary assessment of the entire slide on which the specimen is disposed to alert the cytotechnologist to potentially the most relevant areas of the slide for close inspection, or may be used to rescreen specimens already analyzed by the cytotechnologist.

SUMMARY

In one embodiment, a handheld apparatus for preparing a specimen slide includes a handle, a filter holder assembly coupled to and extending from the handle, and a slide holder assembly coupled to and extending from the handle spaced apart from the filter holder assembly, wherein the slide holder assembly comprises a plurality of positioning members movably coupled to one another, and a slide holder movably coupled to one of the positioning members to allow a slide mounted on the slide holder to make rolling contact with an outward facing surface of a filter mounted on the filter holder assembly. The positioning members are preferably configured to allow the slide holder to be rotated away from the filter holder assembly to facilitate access to the filter holder assembly for removing a filter therefrom or attaching a filter thereto. In an exemplary embodiment, the handle has a grip portion and an extension portion projecting from the grip portion, wherein the respective filter holder assembly and slide holder assembly are attached to the extension portion of the handle at spaced apart locations. In such exemplary embodiment, the filter holder assembly extends from the extension portion of the handle in approximately the same direction as the grip portion extends from the extension portion.

In another embodiment, a handheld apparatus for preparing a specimen slide includes a handle, a filter holder assembly, and a slide holder assembly. The handle has a grip portion, and an extension portion projecting from the grip portion. The filter holder assembly is attached to the extension portion of the handle, and includes a center shaft and a reciprocating cylindrical body disposed around, and slidably coupled to, the center shaft. The slide holder assembly is attached to the extension portion of the handle at a location spaced apart from the filter holder assembly, and includes a plurality of pivotally coupled (e.g., hinged) positioning members and a slide holder movably coupled to a distal-most one of the positioning members relative to the extension portion. The movable connections of the positioning members allow the slide holder to be rotated away from the cylindrical body on the filter holder assembly to facilitate access thereto, e.g., for replacing a filter mounted to the cylindrical member. The movable connections of the positioning members also allow a slide mounted in the slide holder to make rolling contact across a membrane of a filter mounted on the cylindrical body.

In one such embodiment, the filter holder assembly preferably extends from the extension portion of the handle in approximately the same direction as the grip portion extends from the extension portion. In one such embodiment, the center shaft of the filter holder assembly has a proximal end and a distal end relative to the extension portion, and includes a shoulder at the proximal end and a sponge receptacle at the distal end. The sponge receptacle has an opening directed away from the extension portion. The filter holder assembly also includes a spring disposed around the center shaft between the shoulder and the cylindrical body, wherein the spring generates a reciprocating counterforce when the cylindrical body is moved toward the shoulder. The filter holder assembly also includes a sponge disposed in the sponge receptacle, where the sponge is larger than the receptacle and extends partially out of the opening.

In one such embodiment, the cylindrical body of the filter holder assembly has a proximal end and a distal end relative to the extension portion, and a flange at the proximal end. The cylindrical body is configured for a filter to be mounted thereon between the flange and the of the sponge receptacle, with a membrane of the filter disposed at a distal end of the sponge receptacle. The filter holder assembly also includes one or more sealing members disposed around the cylindrical body and configured to form a fluid tight seal between the filter and the cylindrical body. The slide holder assembly is configured to bring a slide mounted in the slide holder into initial contact with a filter mounted on the cylindrical body at an oblique angle, e.g., in a range of about 2.5-7.5 degrees. In some embodiments, the oblique angle is about 5 degrees.

In another embodiment, a handheld apparatus for preparing a specimen slide includes a handle, a filter holder assembly coupled to and extending from the handle, and a slide holder assembly coupled to and extending from the handle, where the slide holder assembly is pivotally jointed to allow a slide mounted in the slide holder assembly to make rolling contact with a filter mounted in the filter holder assembly. The handle also includes a grip portion and an extension portion. In some embodiments, the slide holder assembly is coupled to the grip portion. In other embodiments, the slide holder assembly is coupled to the extension portion. In those embodiments, the filter holder assembly is coupled to the extension portion of the handle at a location spaced apart from the slide holder assembly. The slide holder assembly is configured to allow the slide holder assembly to be rotated away from the cylindrical body to facilitate access to the cylindrical body.

Other and further aspects and features of embodiments of the disclosed inventions will become apparent from the ensuing detailed description in view of the accompanying figures.

BRIEF DESCRIPTION OF THE DRAWINGS

Referring now to the drawings in which like reference numbers represent corresponding parts throughout, and in which.

DETAILED DESCRIPTION OF THE ILLUSTRATED EMBODIMENTS

Figure 1:
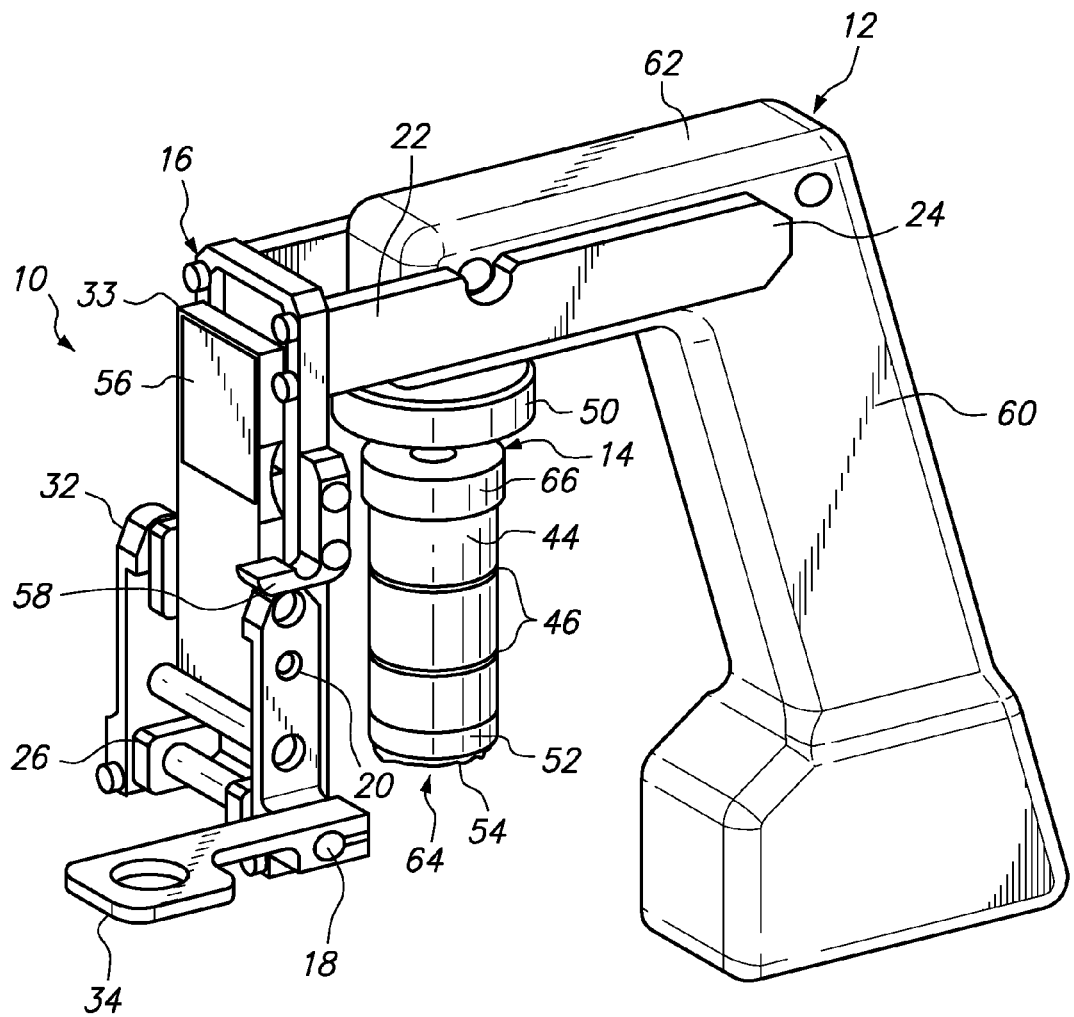
FIG. 1 is a perspective view of a specimen slide preparing device with a slide mounted therein, according to one embodiment.

FIG. 1 illustrates a handheld specimen slide preparing apparatus 10 having a handle 12 and a filter holder assembly 14 and a slide holder assembly 16 attached thereto. The slide holder assembly 16 includes a first hinge 18 and a second hinge 20. The specimen slide preparing apparatus 10 is sized to be held in the hand of a user. The compact size provides portability while reducing cost, complexity, and required laboratory bench space.

The handle 12 has a grip portion 60 and an extension portion 62 projecting approximately orthogonally from the grip portion 60. The slide holder assembly includes an "L" shaped first positioning member 22 having a first end 24 and a second end 26. The first end 22 of the first positioning member 22 is attached to the extension portion 62 of the handle 12. The second end 24 of the first positioning member 22 is located at approximately the same height as a membrane 28 of a filter 30 seated in the filter holder assembly 14. See FIG. 5. The slide holder assembly also includes a second positioning member 32 on which is formed the first and second hinges 18, 20. The first hinge 18 pivotally attaches the second end 26 of the first positioning member 22 to the second positioning member 32. The second hinge 20 pivotally attaches the second positioning member 32 to a slide holder 33.

Figure 2:
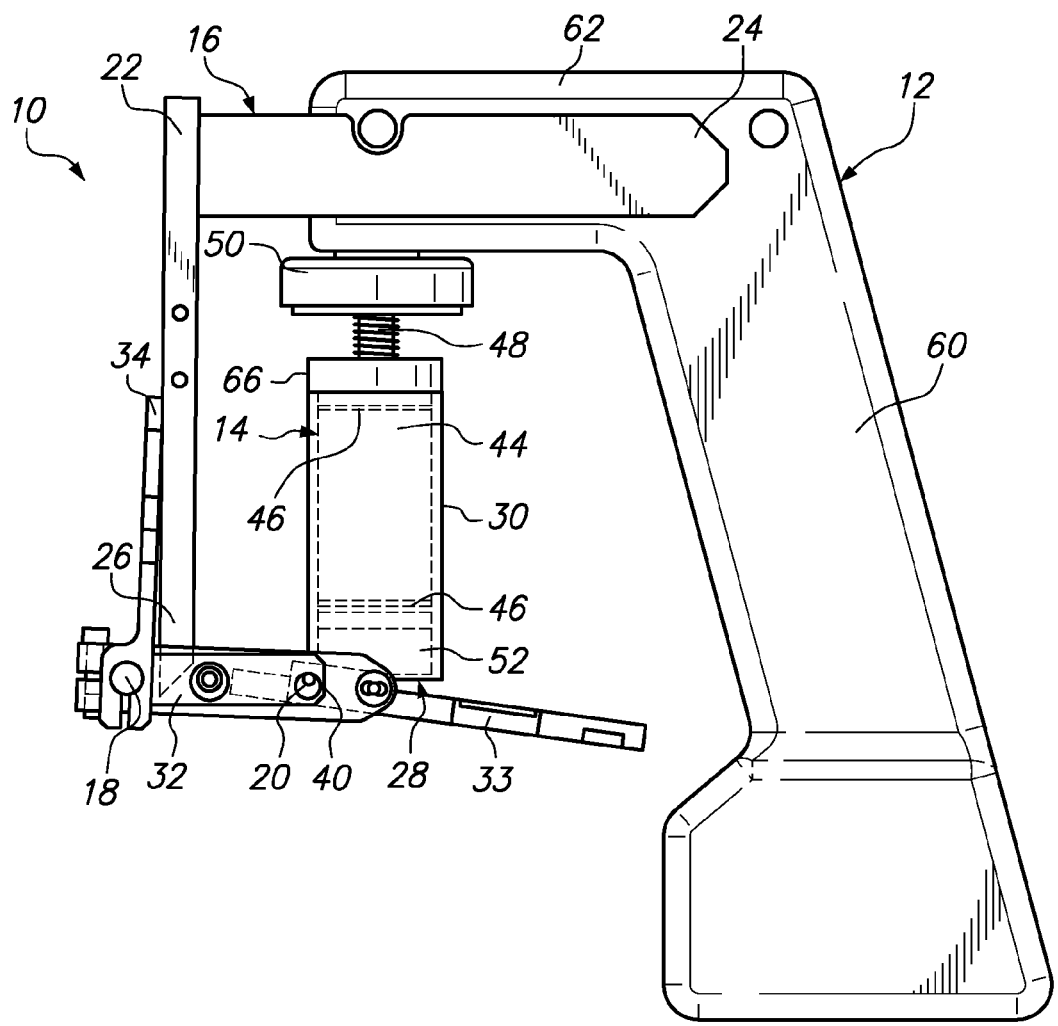
FIG. 2 is a side schematic view of the specimen slide preparing device of FIG. 1 with a slide and a filter mounted therein, showing a slide making initial contact with a filter.

An actuating member in the form of a paddle 34 is attached to the second positioning member 32 and is used to manually rotate the second positioning member 32 from a first position, shown in FIG. 1, to a second position, shown in FIG. 2. To move from the first position to the second position, the second positioning member 32 rotates about the first hinge 18 through an angle of about 270 degrees. When additional pressure is applied to the paddle 34, the second positioning member 32 rotates from the second position to a third position, shown in FIG. 3. To move from the first position to the third position, the second positioning member 32 rotates about the first hinge 18 through an angle in the range of 270-280 degrees. While the first and third positions are end-of-travel positions, the second position is an intermediate position. When pressure is applied to the paddle 34 to rotate the second positioning member 32 from the second position to the third position, the slide holder 33 also rotates about the second hinge 20 from a first position (FIG. 2) to a second position (FIG. 3) through an angle in the range of 0-5 degrees.

Figure 3:
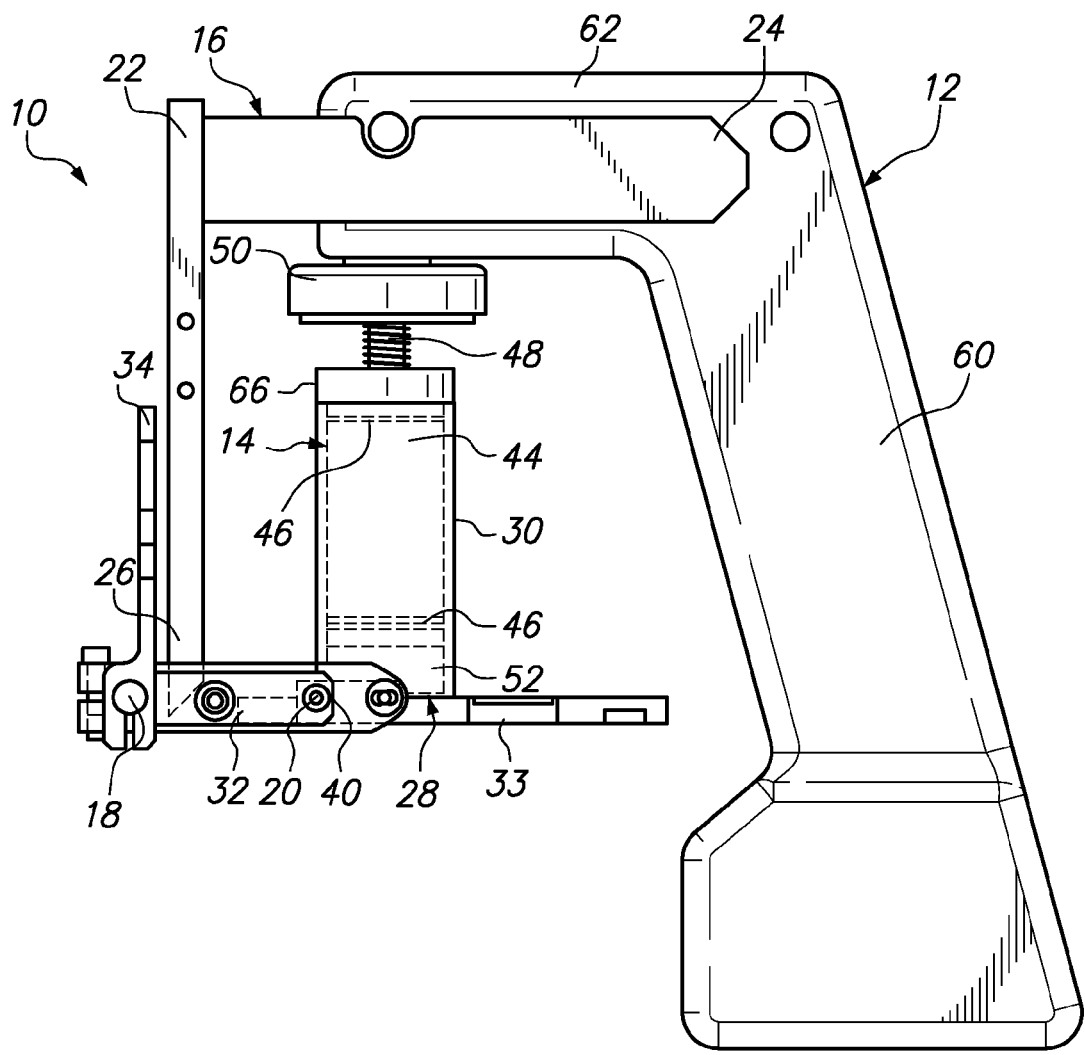
FIG. 3 is another side schematic view of the specimen slide preparing device of FIG. 1 with a slide and a filter mounted therein, showing a slide making complete contract with a filter.
Figure 4:
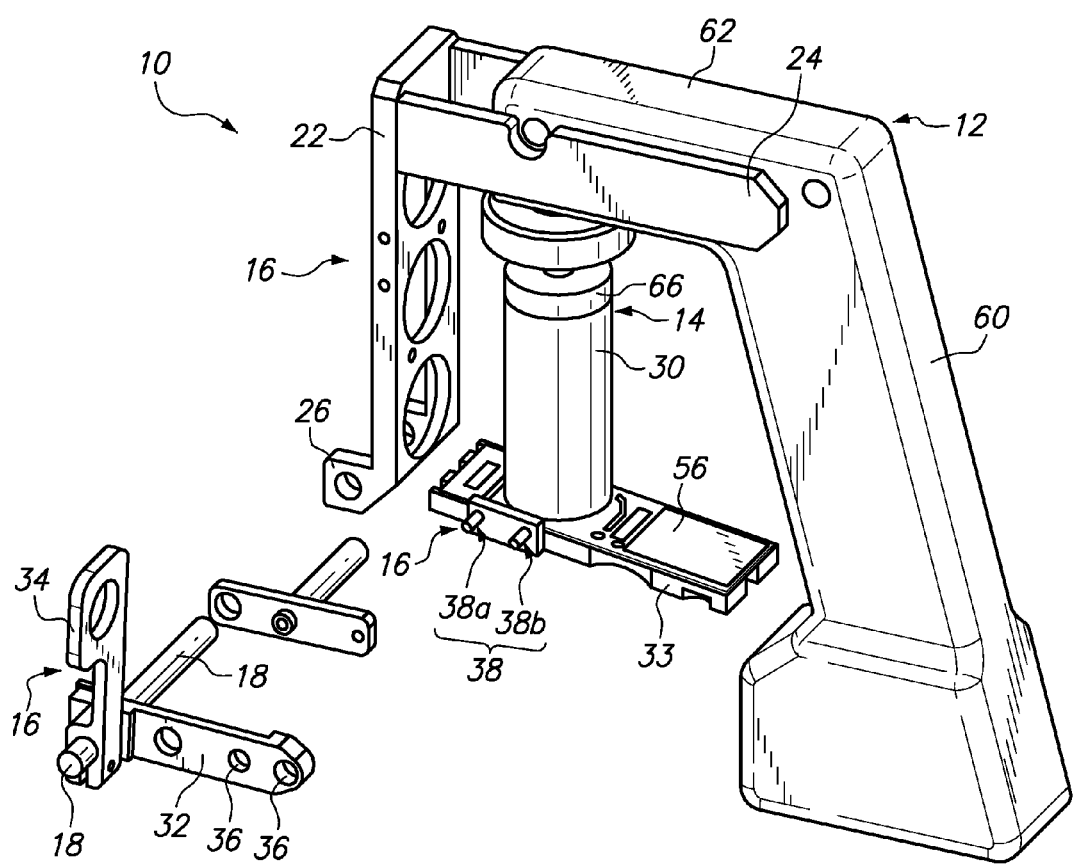
FIG. 4 is an exploded perspective view of the specimen slide preparing device of FIG. 1 with a filter mounted therein, wherein some components have been removed for clarity.

As shown in FIG. 4, four slots 36 are formed in the second positioning member 32, two on each side of the second positioning member 32. The slide holder 33 has four pins 38 disposed thereon in positions corresponding to the positions of the four slots 36 in the second positioning member 32. The pins 38 are inserted into the slots 36 to pivotally attach the slide holder 33 to the second positioning member 32. The slots 36 are slightly larger than the pins 38, thus allowing some movement of the slide holder 33 relative to the second positioning member 32. The pair of pins 38a closer to the first hinge 18 function as pivot pins. The pair of pins 38b farther from the first hinge 18 function as lift pins. They are aligned with the outer edge 40 of the membrane 28 and filter 30 (FIGS. 2 and 3). When the second positioning member 32 is rotated to the second position (FIG. 2) the outer edge 40 and the pivot pins 38a form the second hinge 20 about which the slide holder 33 pivots. The lift pins 38b interact with their slots 36 to minimize sliding movement of the slide holder 33 in the plane of the slide holder 33.

Figure 5:
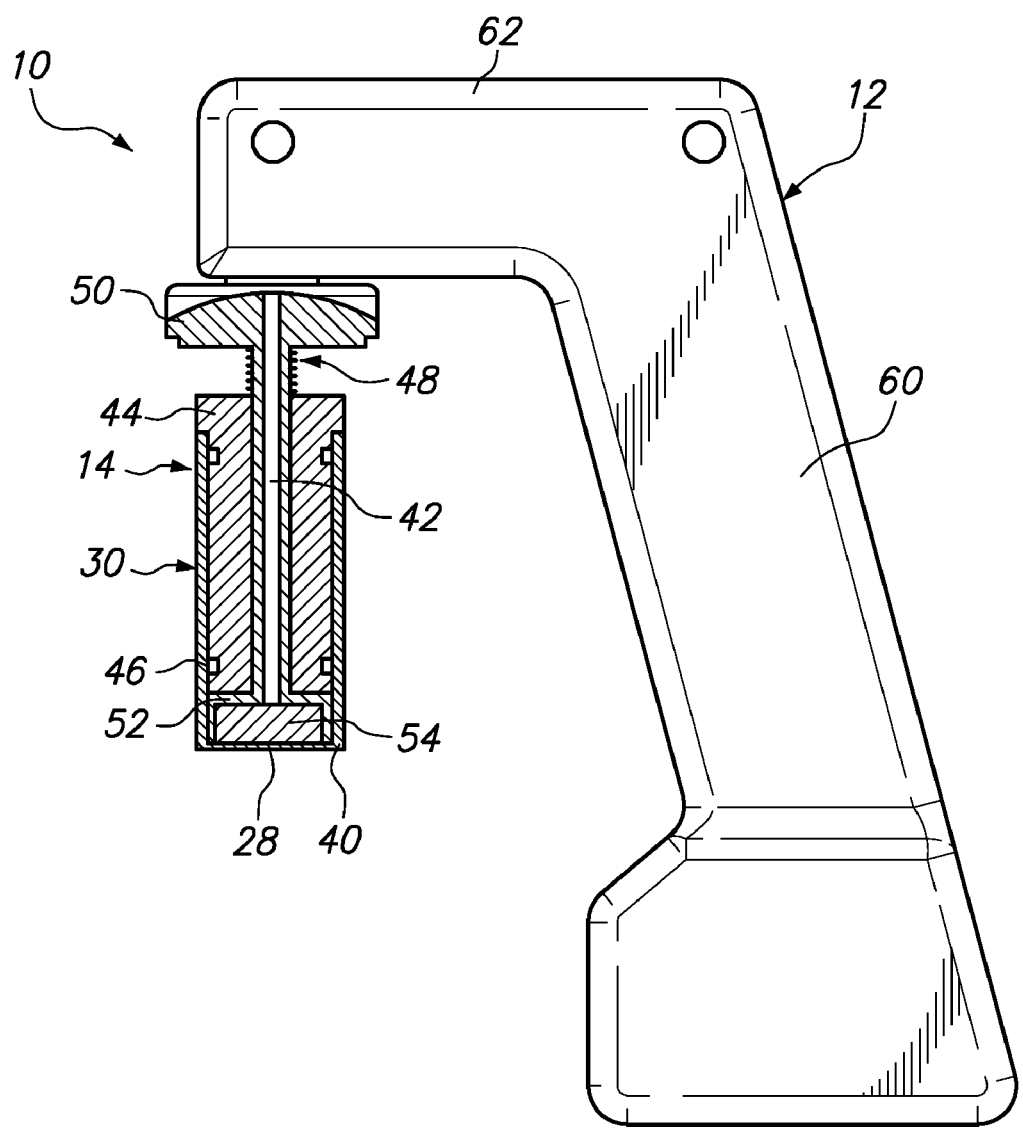
FIG. 5 is a detailed side schematic view of the specimen slide preparing device of FIG. 1 with a filter mounted therein, showing the details of the filter holder assembly.

The filter holder assembly 14 is attached to the extension portion 62 of the handle 12 at a location spaced apart from the slide holder assembly. Referring to FIGS. 1 and 5, the filter holder assembly 14 includes an open center shaft 42 through which a vacuum may be applied to the membrane 28. The filter holder assembly 14 also includes a reciprocating cylindrical body 44 disposed around the center shaft 42 and two O-rings 46 disposed around the cylindrical body 44. The cylindrical body 44 includes a flange 66 configured to mate with a filter 30 mounted on the cylindrical body 44. The cylindrical body 44, the flange 66, and the O-rings 46 secure the filter 30 onto the filter holder assembly 14 with a friction or compression fit. They also form a fluid tight seal between the cylindrical body 44 and the filter 30. A coil spring 48 is disposed around the center shaft 42 on top of the cylindrical body 44.

Above the spring 48, the center shaft 42 widens into a shoulder 50 against which the spring 48 rests. Below the cylindrical body 44, the center shaft 42 widens into a sponge receptacle 52 with an opening 64 directed away from the extension portion 62. A sponge 54 is disposed in the sponge receptacle 52. The sponge 54 is slightly larger than the receptacle 52 and extends partially out of the opening 64. The sponge 54 sits on top of the membrane 28 of a filter 30 fitted onto the cylindrical body 44 of the filter holder assembly 14. The spring 48 biases the cylindrical body 44 and the sponge receptacle 52 against the sponge 54. When the filter 30 is urged toward the shoulder 50 by the upward motion of a slide 56 disposed in the slide holder 33, the spring 48 exerts force on the sponge 54 and creates a dome in the membrane 28 to aid in the transfer of particles from the membrane 28 to the slide 56.

In order to provide for transfer of the particles of interest to the slide 56 without disturbing the spatial distribution thereof, it is desirable that the membrane 28 of the filter 30 initially contacts a small area of the slide 56, forming a predetermined small pre-contact angle between the membrane 28 and a deposition surface of the slide 56, and then gently and gradually enter into complete contact with the slide 56. A rolling motion, similar to that used in fingerprinting, is used to gently and gradually transition from initial contact with a small area to complete contact between the slide 56 and most of the membrane 28.

As depicted in FIG. 2, after a filter 30 with particles of interest collected on its membrane 28 is disposed on the filter holder assembly 14, the second positioning member 32 is rotated about the first hinge 18 to the second position, bringing the slide 56 to a position proximate the membrane 28. Because the bulk of the weight of the slide holder 33 and slide 56 is farthest from the first hinge 18 and the pins 38 are closer to the first hinge 18, gravity will bring the side of the slide holder 33 farthest from the first hinge 18 down and raise the other side of the slide holder 33. Because the pivot pins 38a are closer to first hinge 18 than the lift pins 38b, they will rise more than the lift pins 38b, positioning the slide 56 under the outer edge 40 of the membrane 28 in an orientation slightly offset from horizontal by an oblique angle for initial contact. The oblique angle can be in the range of 2.5-7.5 degrees. In some embodiments, the angle is about 5 degrees.

As shown in FIG. 3, as the second positioning member 32 is rotated about the first hinge 18 to the third position, the slide holder 33 rotates about the second hinge 20 to slowly bring the slide 56 into complete contact with the membrane 28 in a rolling motion. This rolling motion gently displaces any excess liquid from the surface of the membrane and substantially prevents the capture of air bubbles between the membrane 28 and the slide 56 without disturbing the spatial distribution of the particles of interest. The slide holder 33 achieves a more horizontal orientation due to its rotation about the second hinge 20. During this rotation, the interaction of the lift pins 38b with their slots 36 minimizes sliding movement of the slide 56.

With intimate complete contact now achieved between the membrane 28 and the slide 56, the particles of interest captured there-between can be readily transferred, for example with minimal positive pressurization of the filter 30 which slightly domes the membrane into a convex configuration.

As the membrane 28 is thereafter withdrawn from the surface of the slide 56, the reverse procedure takes place by reversing pressure on the paddle 34. The resulting unrolling motion leaves the transferred particles of interest on the slide 56 in an undisturbed monolayer, substantially similar to the spatial distribution created when initially collected against the membrane 28. Using limited initial contact at an oblique angle and rolling and unrolling motions, monolayers of cells can be reliable and repeatably transferred to slides 56 from a plurality of samples by hand. Additionally, because the slide holder 33 is effectively floating at the time of cell transfer on a fluid bearing created at the interface of the membrane 28 and the slide 56, variability in slide thickness, membrane location, and slide/membrane parallelism are readily accommodated.

The particles are collected on the membrane 30 using the filter transfer apparatuses and methods described in the patents listed above. Various elements of filter transfer apparatuses, such as vacuums and control microprocessors programmed to collect a monolayer of particles of interest from specimens suspended in fluid onto the membrane 28 of a filter 30, can be disposed inside of the handle 12 as part of the specimen slide preparing apparatus 10. The vacuum could be applied to the membrane 28 through the open center shaft 42 and controls could be disposed on the handle 12. Such a handheld specimen slide preparing apparatus 10 accommodates variability in the structure of sample vials.

The grip portion 60 of the handle 12 facilitates use by an operator. Also, a latch 58 is disposed on the first positioning member 22 to secure the second positioning member 32 in the first position as shown in FIG. 1. In alternative embodiments, the slide holder assembly may be attached to the grip portion 60 of the handle 12 instead of the extension portion 62.

A slide 56 may be loaded onto the slide holder 33. The slide 56 has tightly toleranced dimensions and chamfered edges to facilitate handling and transfer of the slide 56 and minimize the likelihood of mishandling. In one embodiment, the slide 56 is manufactured from glass and has a width of about one inch, a length of about three inches, and a thickness of about 0.04 inches. One end of the slide 56 is frosted or coated to facilitate marking. The frosted end may have an area of about one square inch. A frosted annulus, defining an area to where the particles of interest are transferred, may also be provided to facilitate manual or automatic scanning of sparse specimens. The bounded specimen area may have an area of about one square inch, substantially equivalent to the surface area of the membrane 28. Additionally, one corner of the frosted end of each slide 56 may be chamfered to a greater degree than the other corners to ensure proper orientation of the slide 56 in the slide holder 33 and proper presentation of the slide 56 to downstream components. While glass microscope slides are typically used for preparing cytological specimens, other analytical elements, such as natural or synthetic material assay strips and the like, are suitable for other analyses and testing, as known by those skilled in the art, and could be employed in the apparatus 10 modified with suitable slide holder assemblies 16.

Various parts of the specimen slide preparing apparatus 10 (e.g., the first positioning member 22, the second positioning member 32, the slide holder assembly 16, etc.) can be machined from metals such as aluminum and polymers such as polyoxymethylene (Delrin®). The handle 12 can be extruded or molded from polymers. The sponge 54 can be obtained from Porex. Various parts are attached with bolts and screws (e.g., the handle 12 and the filter holder assembly 14, the first positioning member 22 and the latch 58, etc.) Others are attached with friction or compression fittings (e.g., the filter holder assembly 14 and the filter 30, the second positioning member 32 in the first position and the latch 58, etc.)

Figure 6:
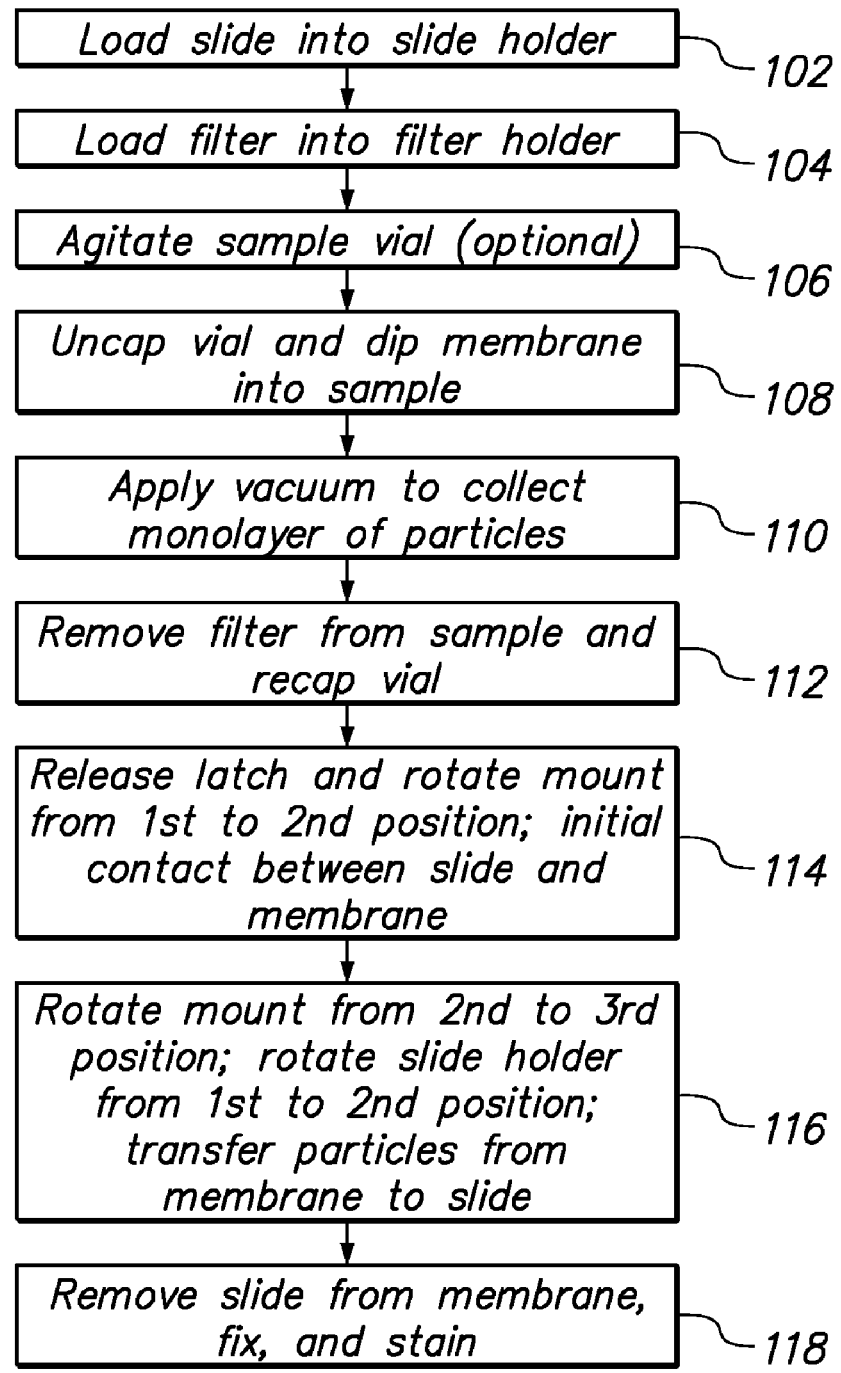
FIG. 6 is a flow chart showing a method of preparing a specimen slide, according to one embodiment.

In use, a slide 56 is loaded into the slide holder 33 with the second positioning member 32 locked in the first position by the latch 58 at step 102 in FIG. 6. At step 104, a filter 30 is loaded onto the filter holder assembly 14. The loading steps 102, 104 may be performed manually with gloved hands to minimize contamination. At step 106, a sample vial is optionally agitated to disperse particles of interest suspended in fluid contained therein. At step 108, the sample vial is uncapped and the membrane 28 of the filter 30 is manually dipped into the fluid. At step 110, a vacuum is applied to the fluid through the membrane 28 to collect a monolayer of particles of interest on the membrane 28. Step 110 may be controlled by a microprocessor programmed to automatically collect such a monolayer using known algorithms. At step 112, the membrane 28 of the filter 30 is removed from the sample vial, which is recapped.

At step 114, the latch 58 is released and the second positioning member 32 is rotated from the first position to the second position, by manually applying pressure to the paddle 34, to bring the slide 56 into a limited initial contact with the outer edge 40 of the membrane 28. At step 116, the second positioning member 32 is rotated from the second position to the third position by manually applying additional pressure to the paddle 34. This additional pressure to the paddle 34 also rotates the slide holder 33 from the first position to the second position, thereby rolling the membrane 28 across the slide 56 to achieve complete contract between the slide 56 and the membrane 28. Further additional pressure to the paddle 34 also compresses the sponge 54 to dome the membrane 28 and facilitate transfer of particles of interest from the membrane 28 to the slide 56. At step 118, the slide 56 is removed from the membrane 28, fixed, and subjected to further processing, e.g. staining.

The disclosed components of the specimen slide preparing apparatus 10 may be manufactured in various sizes, configurations, and materials. Additionally, the apparatus 10 may be used to prepare specimens from various samples, such as gynecologic cytological samples, cells sourced from fine needle aspirates, from mucoid specimens taken from respiratory and gastrointestinal tracts, from body fluids such as serous effusions and urinary and cerebrospinal fluids, from superficial brushings and scrapings from oral cavities, nipple secretions, skin lesions, and eye brushings, and from other sources.

While various embodiments of the disclosed inventions have been shown and described herein, they are presented for purposes of illustration, and not limitation. It will be appreciated by those skilled in the art that various modifications may be made to the illustrated and described embodiments without departing from the scope of the disclosed inventions, which is to be defined only by the following claims and their equivalents.

What is claimed is:

1. A handheld apparatus for preparing a specimen slide, comprising:
   a handle;
   a filter holder assembly coupled to and extending from the handle; and
   a slide holder assembly coupled to and extending from the handle spaced apart from the filter holder assembly, wherein the slide holder assembly comprises a plurality of positioning members movably coupled to one another, and a slide holder movably coupled to one of the positioning members to allow a slide mounted on the slide holder to make rolling contact with an outward facing surface of a filter mounted on the filter holder assembly.

2. The apparatus of claim 1, wherein the positioning members are configured to allow the slide holder to be rotated away from the filter holder assembly to facilitate access to the filter holder assembly for removing a filter therefrom or attaching a filter thereto.

3. The apparatus of claim 1, the handle having a grip portion and an extension portion projecting from the grip portion.

4. The apparatus of claim 3, wherein the respective filter holder assembly and slide holder assembly are attached to the extension portion of the handle at spaced apart locations.

5. The apparatus of claim 4, wherein the filter holder assembly extends from the extension portion of the handle in approximately the same direction as the grip portion extends from the extension portion.

6. The apparatus of claim 4, the filter holder assembly comprising a center shaft and a reciprocating cylindrical body disposed around and slidably coupled to the center shaft, the center shaft having a proximal end and a distal end relative to the extension portion of the handle, the center shaft including a shoulder at the proximal end and a sponge receptacle at the distal end, the sponge receptacle having an opening directed away from the extension portion.

7. The apparatus of claim 6, the filter holder assembly further comprising a spring disposed around the center shaft between the shoulder and the cylindrical body, wherein the spring generates a reciprocating counterforce when the cylindrical body is moved toward the shoulder.

8. The apparatus of claim 7, the filter holder assembly further comprising a sponge disposed in the sponge receptacle, where the sponge is larger than the receptacle and extends partially out of the opening.

9. The apparatus of claim 6, wherein the cylindrical body has a proximal end and a distal end relative to the extension portion of the handle, and wherein the cylindrical body includes a flange at the proximal end, the flange configured for a filter to be mounted thereon between the flange and the sponge receptacle, such that a membrane of the filter is disposed at a distal end of the sponge receptacle.

10. The apparatus of claim 9, the filter holder assembly further including one or more sealing members disposed around the cylindrical body and configured to form a fluid tight seal between the filter and the cylindrical body.

11. The apparatus of claim 6, wherein a first positioning member is coupled to a second positioning member by a first hinge, and the second positioning member is coupled to the slide holder by a second hinge, the first and second hinges respectively configured to allow the slide holder to be rotated away from the cylindrical body to facilitate access to the cylindrical body.

12. The apparatus of claim 11, further comprising an actuating member attached to the slide holder assembly adjacent the first hinge.

13. The apparatus of claim 6, wherein the slide holder assembly is configured to bring a slide mounted in the slide holder into initial contact with a filter membrane mounted on the cylindrical body at an oblique angle.

14. The apparatus of claim 13, wherein the oblique angle is in a range of about 2.5 degrees to about 7.5 degrees.

15. A handheld apparatus for preparing a specimen slide, comprising:
a handle;
a filter holder assembly coupled to and extending from the handle; and
a slide holder assembly coupled to and extending from the handle spaced apart from the filter holder assembly, wherein the slide holder assembly comprises a first positioning member movably coupled to a second positioning member, and a slide holder coupled to the second positioning member by a hinge configured to allow a slide mounted in the slide holder to make rolling contact across a filter membrane of a filter mounted on the filter holder assembly,
wherein the positioning members are configured to allow the slide holder to be rotated away from the filter holder assembly to facilitate access to the filter holder assembly for removing a filter therefrom or attaching a filter thereto.

16. The apparatus of claim 15, the handle having a grip portion and an extension portion projecting from the grip portion, wherein the respective filter holder assembly and slide holder assembly are attached to the extension portion of the handle at spaced apart locations.

17. The apparatus of claim 16, wherein the filter holder assembly extends from the extension portion of the handle in approximately the same direction as the grip portion extends from the extension portion.

18. A handheld apparatus for preparing a specimen slide, comprising, a handle;
a filter holder assembly coupled to the handle; and
a slide holder assembly coupled to the handle,
wherein the filter holder assembly includes a center shaft and a reciprocating cylindrical body disposed around and slidably coupled to the center shaft, the cylindrical body configured for removably coupling a filter body, and
wherein the slide holder assembly includes a plurality of pivotally coupled positioning members and a slide holder movably coupled to one of the positioning members such that the positioning members allow the slide holder to be rotated away from the cylindrical body on the filter holder assembly to facilitate access thereto, and further allow a slide mounted in the slide holder to make rolling contact across a membrane of a filter mounted on the cylindrical body.

19. The apparatus of claim 18, wherein the center shaft of the filter holder assembly has a proximal end and a distal end relative to the extension portion, and includes a shoulder at the proximal end and a sponge receptacle at the distal end, the sponge receptacle having an opening directed away from the extension portion, the filter holder assembly further comprising a spring disposed around the center shaft between the shoulder and the cylindrical body, wherein the spring generates a reciprocating counterforce when the cylindrical body is moved toward the shoulder.

20. The apparatus of claim 19, the filter holder assembly further comprising a sponge disposed in the sponge receptacle, where the sponge is larger than the receptacle and extends partially out of the opening.

21. A handheld apparatus for preparing a specimen slide, comprising:
a handle;
a filter holder assembly coupled to and extending from the handle; and
a slide holder assembly, wherein the slide holder assembly allows a slide mounted on the slide holder to make contact with a filter mounted on the filter holder assembly.

22. The apparatus of claim 21, wherein the slide holder assembly comprises a plurality of positioning members movably coupled to one another, the slide holder being movably coupled to one of the positioning members to allow a slide mounted on the slide holder to make rolling contact with a filter mounted on the filter holder assembly.

23. The apparatus of claim 21, the handle having a grip portion and an extension portion projecting from the grip portion, wherein the respective filter holder assembly and slide holder assembly are attached to the extension portion of the handle at spaced apart locations.

24. The apparatus of claim 23, wherein the filter holder assembly extends from the extension portion of the handle in approximately the same direction as the grip portion extends from the extension portion.

25. The apparatus of claim 24, the filter holder assembly comprising a center shaft and a reciprocating cylindrical body disposed around and slidably coupled to the center shaft, the center shaft having a proximal end and a distal end relative to the extension portion of the handle, the center shaft including a shoulder at the proximal end and a sponge receptacle at the distal end, the sponge receptacle having an opening directed away from the extension portion.

26. The apparatus of claim 25, the filter holder assembly further comprising a spring disposed around the center shaft between the shoulder and the cylindrical body, wherein the spring generates a reciprocating counterforce when the cylindrical body is moved toward the shoulder.

27. The apparatus of claim 26, the filter holder assembly further comprising a sponge disposed in the sponge receptacle, where the sponge is larger than the receptacle and extends partially out of the opening.

28. The apparatus of claim 25, wherein the cylindrical body has a proximal end and a distal end relative to the extension portion of the handle, and wherein the cylindrical body includes a flange at the proximal end, the flange configured for a filter to be mounted thereon between the flange and the sponge receptacle, such that a membrane of the filter is disposed at a distal end of the sponge receptacle.

29. The apparatus of claim 28, the filter holder assembly further including one or more sealing members disposed around the cylindrical body and configured to form a fluid tight seal between the filter and the cylindrical body.

30. The apparatus of claim 25, wherein the slide holder is attached to the extension portion of the handle via one or more rotatably coupled members configured to allow the slide holder to be rotated away from the cylindrical body in order to facilitate access to the cylindrical body.

31. The apparatus of claim 25, wherein the slide holder assembly is configured to bring a slide mounted in the slide holder into initial contact with a filter membrane mounted on the cylindrical body at an oblique angle.

32. The apparatus of claim 31, wherein the oblique angle is in a range of about 2.5 degrees to about 7.5 degrees.

* * * * *